(12) United States Patent
Shiomitsu et al.

(10) Patent No.: US 9,238,384 B2
(45) Date of Patent: Jan. 19, 2016

(54) METHOD OF MANUFACTURING MICRONEEDLE

(71) Applicant: TOPPAN PRINTING CO., LTD., Tokyo (JP)

(72) Inventors: Kazuhiko Shiomitsu, Tokyo (JP); Hiroshi Sugimura, Tokyo (JP); Toshiaki Kurosu, Tokyo (JP); Gaku Suzuki, Tokyo (JP); Takao Tomono, Tokyo (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 109 days.

(21) Appl. No.: 13/752,959

(22) Filed: Jan. 29, 2013

(65) Prior Publication Data

US 2013/0140267 A1 Jun. 6, 2013

Related U.S. Application Data

(60) Continuation of application No. 12/749,001, filed on Mar. 29, 2010, now Pat. No. 8,377,364, which is a division of application No. 12/318,629, filed on Jan. 2, 2009, now abandoned, which is a continuation of application No. PCT/JP2007/063398, filed on Jul. 4, 2007.

(30) Foreign Application Priority Data

Jul. 4, 2006 (JP) ................................ 2006-184198
Oct. 31, 2006 (JP) ................................ 2006-295538
Dec. 4, 2006 (JP) ................................ 2006-326952

(51) Int. Cl.
*B44C 1/20* (2006.01)
*B44C 1/22* (2006.01)
(Continued)

(52) U.S. Cl.
CPC ............ *B44C 1/227* (2013.01); *A61M 37/0015* (2013.01); *B29C 33/42* (2013.01);
(Continued)

(58) Field of Classification Search
USPC .......... 216/10, 11, 12, 2, 27, 41, 42; 250/216, 250/234; 264/220; 313/309, 351, 366; 355/71; 428/143; 430/314, 320; 438/20, 29, 52, 637, 694, 703, 706; 439/886; 604/173, 191, 198, 22, 272, 604/46; 73/105; 850/32, 40, 53, 56, 57, 59, 850/60, 9
See application file for complete search history.

(56) References Cited

U.S. PATENT DOCUMENTS 3,970,887 A * 7/1976 Smith et al. ..................... 313/309
4,513,308 A * 4/1985 Greene et al. ................... 313/351
(Continued)

FOREIGN PATENT DOCUMENTS

JP 10-092300 * 4/1998 ............... H01J 9/02
JP 2000-513971 10/2000
(Continued)

OTHER PUBLICATIONS

Machine translation of JP10-092300 pulled May 7, 2015.*
(Continued)

*Primary Examiner* — Duy Deo
*Assistant Examiner* — Erin Bergner

(57) ABSTRACT

The invention discloses a method of manufacturing a microneedle including the steps of forming an island etching mask having thickness distribution on a substrate, and processing the substrate into a needle by taking advantage of a difference in etching rates between the etching mask and the substrate. The invention enables to readily control a point angle and height of the manufactured needle.

14 Claims, 15 Drawing Sheets

(51) Int. Cl.
  *A61M 37/00* (2006.01)
  *B29C 33/42* (2006.01)
  *B81C 1/00* (2006.01)

(52) U.S. Cl.
  CPC ...... *B81C1/00111* (2013.01); *A61M 2037/003* (2013.01); *A61M 2037/0038* (2013.01); *A61M 2037/0046* (2013.01); *A61M 2037/0053* (2013.01); *B81B 2201/055* (2013.01); *B81C 2201/0198* (2013.01)

(56) References Cited

U.S. PATENT DOCUMENTS

| | | | |
|---|---|---|---|
| 5,312,514 A * | 5/1994 | Kumar | 216/11 |
| 5,705,025 A | 1/1998 | Dietrich et al. | |
| 5,811,020 A | 9/1998 | Alwan | |
| 6,057,236 A * | 5/2000 | Clevenger et al. | 438/680 |
| 6,174,449 B1 | 1/2001 | Alwan et al. | |
| 6,183,434 B1 | 2/2001 | Eppstein | |
| 6,334,856 B1 | 1/2002 | Allen et al. | |
| 6,338,938 B1 | 1/2002 | Lahaug | |
| 6,406,638 B1 | 6/2002 | Stoeber et al. | |
| 6,780,491 B1 | 8/2004 | Cathey et al. | |
| 6,790,372 B2 | 9/2004 | Roy et al. | |
| 6,815,360 B1 | 11/2004 | Canham et al. | |
| 6,962,772 B2 | 11/2005 | Liu et al. | |
| 7,132,054 B1 | 11/2006 | Kravitz et al. | |
| 2002/0155737 A1* | 10/2002 | Roy et al. | 439/66 |
| 2004/0060902 A1 | 4/2004 | Evans et al. | |
| 2004/0126707 A1 | 7/2004 | Liu et al. | |
| 2004/0186419 A1 | 9/2004 | Cho | |
| 2005/0209565 A1 | 9/2005 | Yuzhakov et al. | |
| 2006/0030812 A1 | 2/2006 | Golubovic-Liakopoulos | |

FOREIGN PATENT DOCUMENTS

| | | |
|---|---|---|
| JP | 2002-79499 | 3/2002 |
| JP | 2002-239014 | 8/2002 |
| JP | 2004-114552 | 4/2004 |
| JP | 2004-195599 | 7/2004 |
| JP | 2005-21677 | 1/2005 |
| JP | 2005-199392 | 7/2005 |
| JP | 2005-246595 | 9/2005 |
| JP | 2005-249809 | 9/2005 |
| JP | 2006-82999 | 3/2006 |
| JP | 2006-96002 | 4/2006 |
| WO | 2004/078668 | 9/2004 |
| WO | 2005/044139 A2 | 5/2005 |
| WO | 2007/147671 | 12/2007 |

OTHER PUBLICATIONS

International Search Report mailed on Aug. 14, 2007 in connection with International Application No. PCT/JP2007/063398.
Japanese Notice of Reasons for Rejection Office Action issued on Oct. 28, 2008 in corresponding Japanese Patent Application No. 2008-504552.
Notification of Transmittals of Translation of the International Preliminary Report on Patentability mailed Jan. 29, 2009, including International Preliminary Report on Patentability and Written Opinion of the International Searching Authority in corresponding priority International Application No. PCT/JP2007/063398.
US Office Action mailed on Nov. 30, 2009 in parent U.S. Appl. No. 12/318,629.
US Office Action mailed on Jul. 10, 2009 in parent U.S. Appl. No. 12/318,629.
US Restriction Office Action mailed Apr. 27, 2009 in parent U.S. Appl. No. 12/318,629.
Japanese Office Action issued Apr. 17, 2012 in corresponding Japanese Patent Application No. 2008-215616 (2 pages) (3 pages English translation).
US Office Action mailed on Jan. 18, 2012 in parent U.S. Appl. No. 12/749,001 (7 pages).
US Office Action mailed on Apr. 16, 2012 in parent U.S. Appl. No. 12/749,001 (7 page).
US Notice of Allowance mailed on Oct. 15, 2012 in parent U.S. Appl. No. 12/749,001 (7 pages).
U.S. Appl. No. 12/749,001, filed Mar. 9, 2010, Kazuhiko Shiomitsu, Toppan Printing Co., Ltd.
Extended European Search Report dated May 28, 2014 in corresponding European Patent Application No. 07768150.0 (6 pages).
Gonzalo Cabodevila, Bruno Lepioufle, Hiroyuki Fujita; "*Arrayed Micro Needles for Mechanical Gene Insertion*"; Biomedical Applications of Micro-and Nanoengineering, Dan V. Nicolau, Abraham P. Lee, Editors, Proceedings of SPIE vol. 4937 (2002), (Jun. 30, 2003) pp. 90-97.
Japanese Office Action mailed Mar. 4, 2014 in corresponding Japanese Patent Application No. 2013-080571 (2 pages) (2 pages English Translation).
U.S. Appl. No. 12/318,629, filed Jan. 2, 2009, Kazuhiko Shiomitsu, Toppan Printing Co., Ltd.
U.S. Appl. No. 12/749,001, filed Mar. 29, 2010, Kazuhiko Shiomitsu, Toppan Printing Co., Ltd.

\* cited by examiner

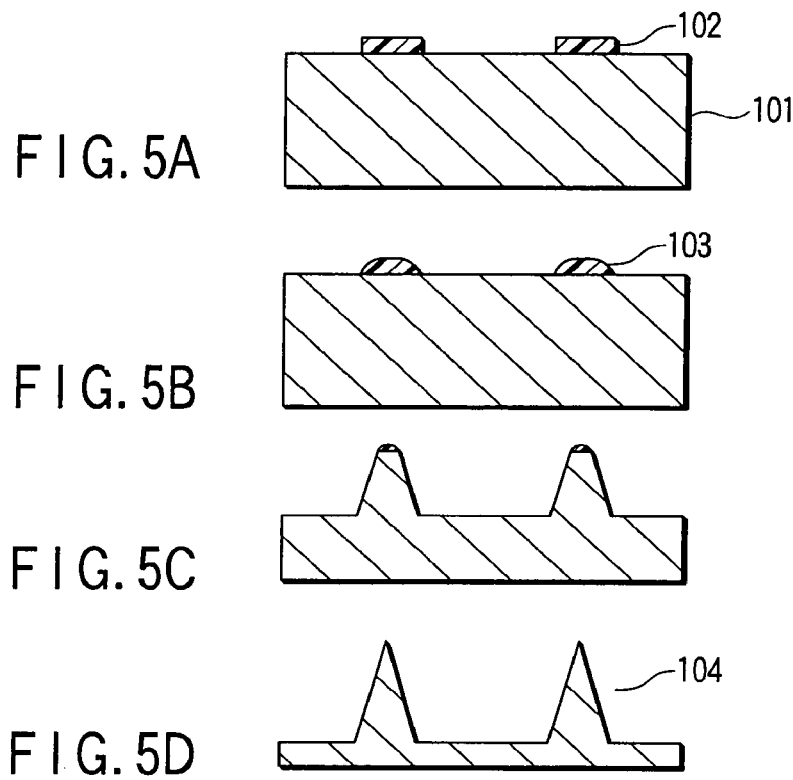
FIG. 5A
FIG. 5B
FIG. 5C
FIG. 5D
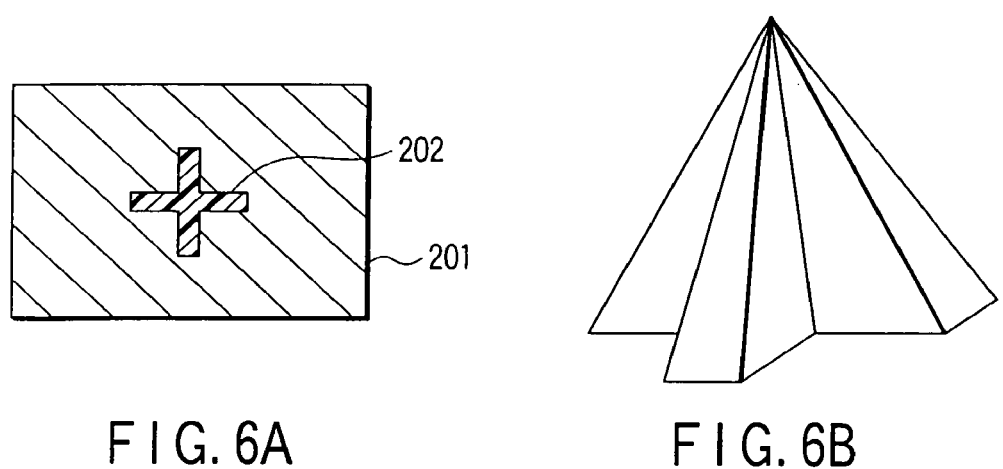
FIG. 6A
FIG. 6B

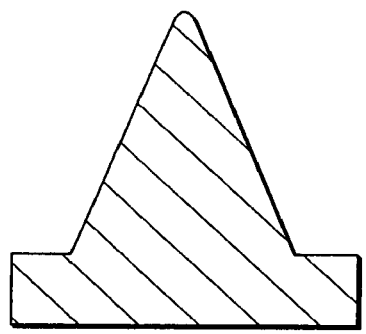
F I G. 22A
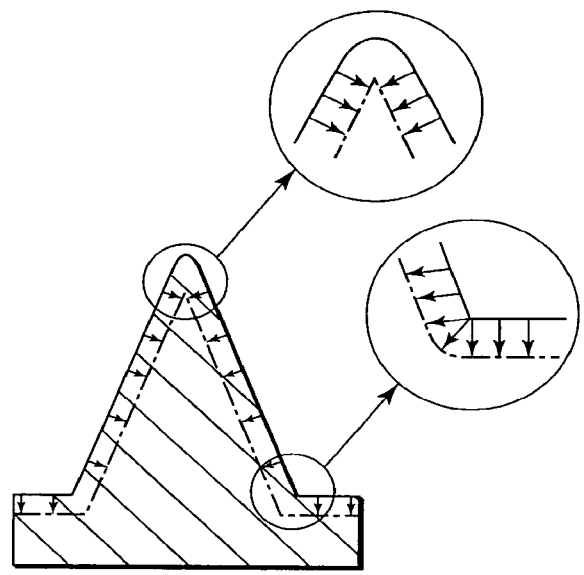
F I G. 22B
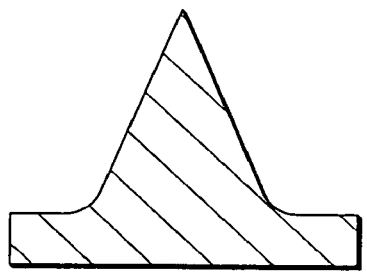
F I G. 22C

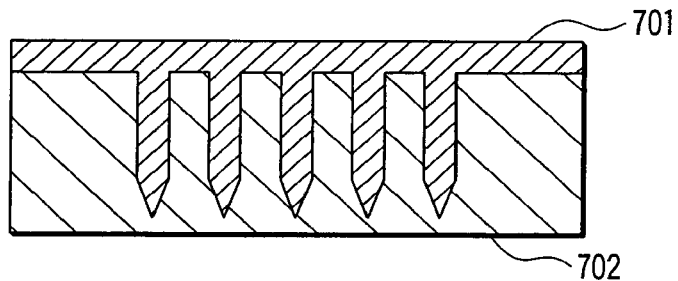
F I G. 23A
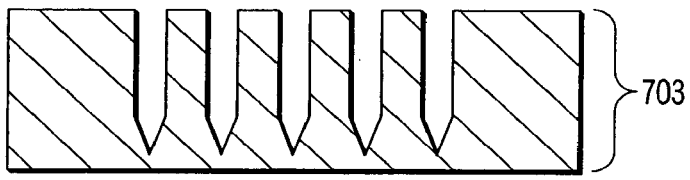
F I G. 23B
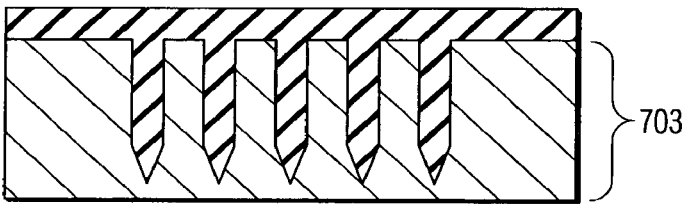
F I G. 23C
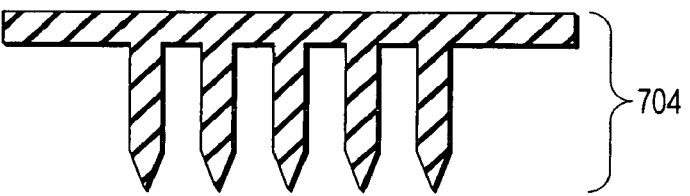
F I G. 23D F I G. 24A 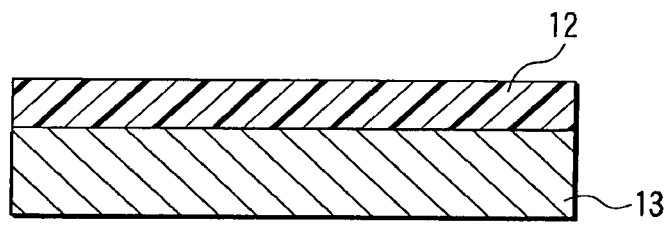
Patterning, exposure and development
F I G. 24B 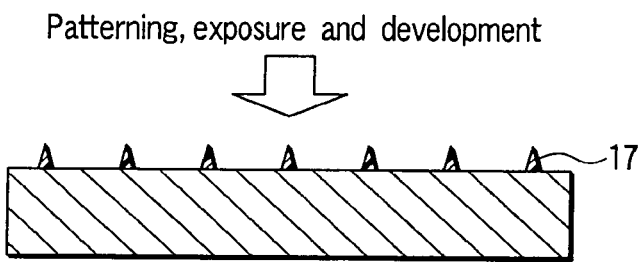
Reactive ion etching
F I G. 24C 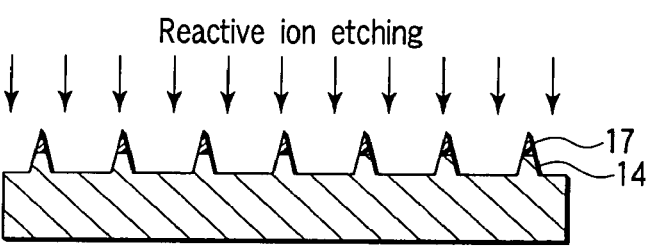
F I G. 24D 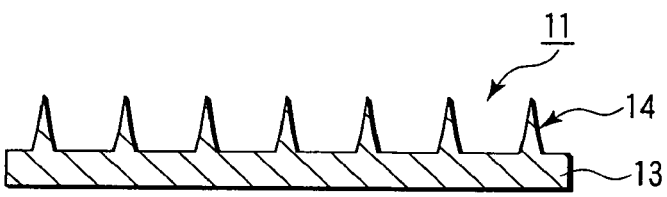
F I G. 24E 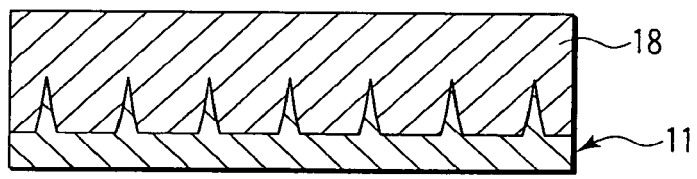
F I G. 24F 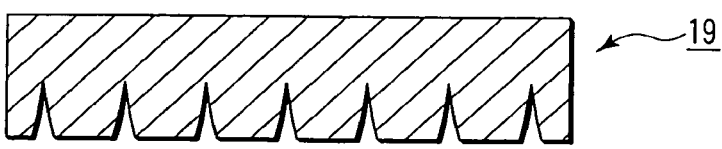

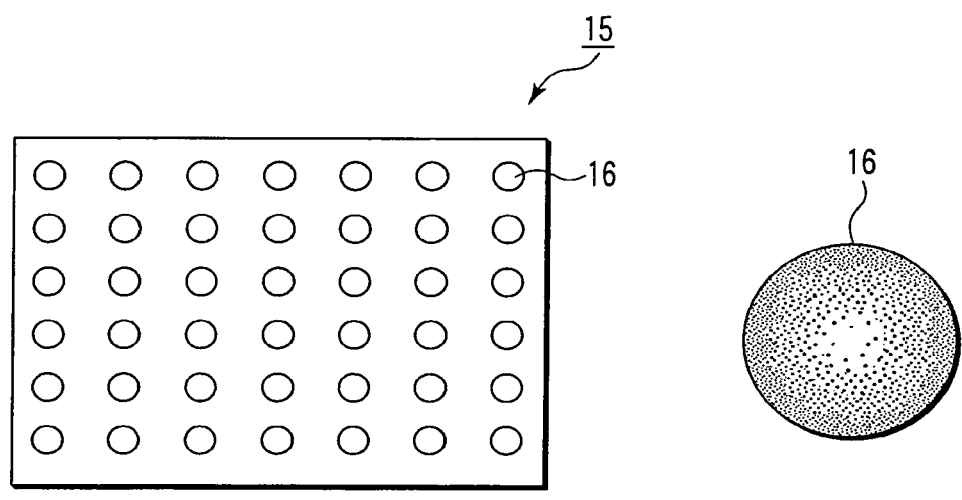
F I G. 25A         F I G. 25B

METHOD OF MANUFACTURING MICRONEEDLE

CROSS REFERENCE TO RELATED APPLICATIONS

This application is a Continuation application of U.S. patent application Ser. No. 12/749,001 filed Mar. 29, 2010, which is a divisional application of U.S. patent application Ser. No. 12/318,629 filed Jan. 2, 2009, which is a Continuation application of PCT Application No. PCT/JP2007/063398, filed Jul. 4, 2007, which was published under PCT Article 21(2) in Japanese, the entire contents of all of which are incorporated herein by reference.

This application is based upon and claims the benefit of priority from prior Japanese Patent Applications No. 2006-184198, filed Jul. 4, 2006; No. 2006-295538, filed Oct. 31, 2006; and No. 2006-326952, filed Dec. 4, 2006, the entire contents of all of which are incorporated herein by reference.

BACKGROUND OF THE INVENTION

1. Field of the Invention

The present invention relates to a method of manufacturing a microneedle.

2. Description of the Related Art

Percutaneous absorption has been known as one of the methods for administering a drug by permitting it to permeate through the skin. In this method, a liquid or gel of the drug is applied on the surface of a living body such as the skin or mucous membrane.

This method is noninvasive, and makes it possible to simply administer the drug without giving pain to the human body. However, the applied drug is liable to be removed by perspiration or external contact. Another problem may arise in terms of safety since skin failure occurs by long-term administration. In addition, the drug is hardly absorbed in the body merely by applying it on the surface of the body when the drug to be administered has a high molecular weight or the drug is water soluble, and percutaneous absorption of such drug is difficult.

Accordingly, a noticed method is to directly inject the drug beneath the skin by perforating the skin using a microneedle array having many needles of micron order in order to permit the drug to be efficiently absorbed into the body. This method enables simple subcutaneous administration without using any special devices (see U.S. Pat. No. 6,183,434).

The microneedle used in this method is required to have sufficient fineness and point angle for perforating the skin, and a sufficient length for permitting the drug solution to be permeated under the skin. Consequently, it is thought to be desirable that the needle diameter is from several μm to 100 μm, and the needle length is selected so that the needle penetrates through corneum that is an outermost layer of the skin while the needle does not reach a nerve layer, or specifically from scores of μm to hundreds of μm. The material constituting the needle is required to be harmless to the human body even when the needle is broken and left behind in the body. Materials considered to be promising include medical use silicone resins and biocompatible resins such as maltose, polylactate and dextran resins (see Jpn. Pat. Appln. KOKAI Publication No. 2005-21677).

For mass production of needles having such a fine structure with a low production cost, transcription molding methods represented by injection molding method, imprint method and casting method are effective. However, a mold having inversed projections and recesses of a desired shape is necessary for molding by any of the above-mentioned methods, and a quite complicated production process is required for forming a structure that is necessary to have a high aspect ratio (a ratio of the height or depth to the diameter of the structure) and an acute tip as the microneedle.

In a proposed method of manufacturing the microneedle, the tip of the needle is sharpened by anisotropic wet etching of a single crystal material such as a silicon wafer by taking advantage of a difference in etching rates between respective crystal orientations of the singe crystal. However, a strict control of the anisotropic wet etching time is necessary for sharpening the tip of the needle, and a high degree of processing technology becomes necessary (Jpn. Pat. Appln. KOKAI Publication No. 2002-79499).

Other proposed methods include controlling the point angle of the needle by changing the light exposure value while an exposure mask is moved (see Jpn. Pat. Appln. KOKAI Publication No. 2005-246595), or combining wet etching using a chemical solution and plasma etching (see Jpn. Pat. Appln. KOKAI Publication No. 2002-239014).

Another method of manufacturing microneedles to form a microneedle patch includes the steps of forming tips of the microneedles by isotropic etching under a resist mask, and forming microneedles with a desired height by anisotropic etching (see Jpn. Pat. Appln. KOKAI Publication No. 2005-199392).

However, the above-mentioned manufacturing methods involve a problem in the cost and time since the methods include many complicated steps of forming a thermal oxide layer, applying a resist, forming a mask pattern by photolithography, applying isotropic etching, applying anisotropic etching, removing a sidewall deposit layer, and applying gradient etching.

While the microneedle is required to be uniformly formed particularly with respect to the height since the microneedle should reliably arrive at body tissues such as the epidermis, it is difficult to form the microneedle with high accuracy by the above-mentioned methods.

A special exposure apparatus that is not usually used, a high precision machining technique and a complicated manufacturing process are often needed for satisfying the structural requirement of the microneedle, since a high aspect ratio as well as sharpening the tip are necessary in the conventional methods for manufacturing the microneedle. It is another problem that stripped pieces of the mask contaminate around the mask as etching advances.

BRIEF SUMMARY OF THE INVENTION

An object of the invention is to provide a method of manufacturing a needle capable of readily controlling the point angle and height without using any complicated manufacturing process or special manufacturing apparatus.

The invention provides a method of manufacturing a microneedle characterized by comprising the steps of: forming an island etching mask having thickness distribution on a substrate; and processing the substrate into a needle by taking advantage of a difference in etching rates between the etching mask and the substrate.

In the invention, it is preferable to form an array of etching masks on the substrate.

The invention may comprise the steps of: providing a recess having depth distribution on the substrate; and forming the island etching mask having thickness distribution so as to cover at least a part of the recess.

In the invention, the etching mask may be formed so as to cover the recess and a part of a periphery of the recess, or may be formed so as to cover an entire surface of the substrate including the recess.

In the invention, an opening may be provided at a position corresponding to the recess of the etching mask, or the opening may be formed so as to be displaced from the recess.

The invention may comprise the steps of: forming an island etching mask on the substrate; deforming the etching mask so as to have thickness distribution; and processing the substrate into a needle by taking advantage of a difference in etching rates between the etching mask and the substrate.

In the invention, the island etching mask formed on the substrate is deformed so as to have thickness distribution by allowing the etching mask to reflow.

In the invention, the island etching mask may be formed on the substrate by ejecting a droplet prepared by dissolving an etching mask material in a solvent or by ejecting a droplet prepared by heating and melting the etching mask material, and the etching mask may be deformed so as to have thickness distribution by allowing the solvent to evaporate or by allowing the etching mask material to solidify.

The invention may comprise the steps of: forming a hole on the substrate; filling the hole with a filler; forming an island etching mask on a side of the substrate where the hole is formed; deforming the etching mask in a thickness direction; etching the substrate to process into a needle; and removing the filler.

The invention may comprise the steps of: forming a hole on the substrate; forming an island etching mask on a side of the substrate opposed to the side where the hole is formed; deforming the etching mask in a thickness direction; and etching the substrate to process into a needle.

In these methods, the hole may be a non-penetrated hole or a penetrated hole. Further, a position of the etching mask may be aligned with a position of the hole, or a position of the etching mask may be displaced from a position of the hole.

In the invention, the etching mask may be formed into a shape having a periphery a part of which is inwardly depressed.

In the invention, an etching selectivity ratio defined by dividing the etching rate of the substrate by the etching rate of the etching mask is preferably set to 1 or more and 100 or less. In addition, an etching condition may be changed so that an etching selectivity ratio is changed on the way of etching.

The invention may comprise the steps of: forming a resist layer on the substrate; exposing the resist layer with light using any one of exposure through a mask using a halftone dot pattern, exposure through a mask using a gray scale pattern, multiple laser exposure and inclined exposure; developing the resist layer to form the island etching mask having thickness distribution on the substrate; and processing the substrate into a needle by taking advantage of the difference in etching rates between the etching mask and the substrate.

In the invention, anisotropic etching is used for the etching. The anisotropic etching includes ion etching, reactive ion etching, ion-beam etching and reactive ion-beam etching.

In the invention, after the microneedle is formed, the microneedle may be subjected to isotropic etching.

In the invention, a replica mold for manufacturing a microneedle may be manufactured by transcription using the manufactured microneedle as a master mold. In this case, the transcription can be performed by using a plated metal, resin or ceramic.

The invention also includes a microneedle manufactured by the above-mentioned method. The invention also includes a microneedle manufactured by using the replica mold for manufacturing the microneedle. The microneedle of the invention is preferably formed of a biocompatible material.

BRIEF DESCRIPTION OF THE SEVERAL VIEWS OF THE DRAWING

FIGS. 5A to 5D show cross-sectional views showing a method of manufacturing the microneedle of the invention.

FIGS. 6A and 6B show an example of a needle which can be formed by the method of manufacturing the microneedle according to the invention.

FIGS. 22A to 22C show cross-sectional views showing a method of manufacturing a microneedle according to the invention.

FIGS. 23A to 23D show cross-sectional views showing steps of a method of manufacturing a microneedle using a transcription process according to the invention.

FIGS. 24A to 24F show cross-sectional views showing a method of manufacturing a microneedle according to the invention.

FIGS. 25A and 25B show cross-sectional views showing a method of manufacturing a microneedle according to the invention.

DETAILED DESCRIPTION OF THE INVENTION

A method of manufacturing a microneedle according to an embodiment of the invention will be described with reference to FIGS. 1A to 1F.

<Process for Providing a Recess Having Depth Distribution on a Substrate>

A recess having depth distribution is formed on a substrate at the position to the position for forming the needles.

Any materials may be used for the substrate as long as they can be processed by wet etching, plasma etching and blast treatment. Specific examples of the material include silicon, a metal such as aluminum and stainless steel, and a synthetic resin such as polycarbonate, polystyrene, acrylic resin and fluorinated resin.

Examples of the method for forming the recess include wet etching, laser machining, reactive ion etching and focused ion beam. Since the final shape and diameter of the needle depend on the shape and diameter of the recess formed, the shape of the recess is determined depending on the shape of the desired needle.

For example, the point angle and height of the needle that is finally manufactured may be controlled by controlling the shape of the bottom of the recess. The point angle tends to be sharpened when the bottom of the recess has an acute angle, while the height of the needle tends to be increased when the recess is deep.

Figure 1A:
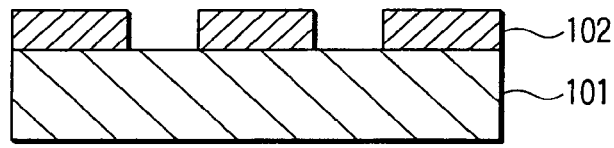
FIGS. 1A to 1F show cross-sectional views showing a method of manufacturing a microneedle of the invention.

A case of providing the recess by etching will be described. First, etching mask is formed on the substrate (FIG. 1A).

The etching mask may be formed using a resist, a hard mask having a pattern of opening on a metal film, or a metal film, an organometallic film, a silicone oxide film or silicon nitride film directly formed on the substrate by CVD (chemical vapor deposition) or PVD (physical vapor deposition). Alternatively, a silicon oxide film formed by thermal oxidation may be used when the substrate is silicon.

When needles are to be formed, it is possible to form an array having any number of needles at any pitch by appropriately designing a pattern layout of the etching mask to be formed.

Figure 1B:
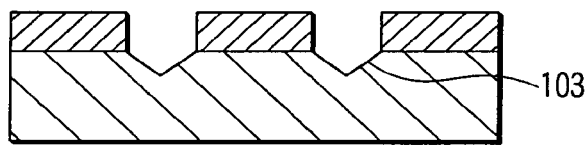

A recess 103 having depth distribution is formed by etching the substrate exposed out of the etching mask (FIG. 1B). The etching mask 102 is removed after the recess is formed.

In this case, the shape of the bottom of the recess may be determined by the difference in the etching rate depending on the crystal orientation of the substrate or by the etching selectivity ratio between the etching mask and substrate. As described above, the point angle and height of the needle to be finally manufactured may be controlled by controlling the shape of the bottom of the recess.

<Process for Forming an Etching Mask Having Thickness Distribution>

Figure 1C:
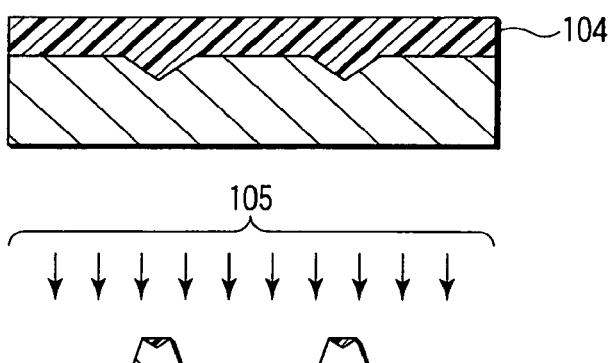

An etching mask having thickness distribution is then formed on the substrate so that the mask covers at least a part of the recess. For example, if an etching mask is formed over the entire surface of the substrate, the etching mask 104 filled in the recess 103 has thickness distribution (FIG. 1C). Accordingly, the etching mask 104 is not necessarily patterned.

<Process for Etching the Substrate>

Figure 1D:
Figure 1E:
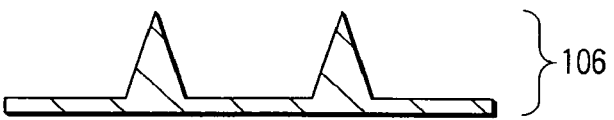

The entire surface of the substrate 101 on which the etching mask 104 is formed is etched to form a microneedle 106 (FIGS. 1D and 1E). When silicon is used for the substrate 101, the substrate is subjected to anisotropic etching using a fluorine-based gas.

When the etching starts from the state shown in FIG. 1C, the etching mask 104 is etched with the same thickness on the entire surface, the top surface of the substrate 101 is exposed, and the etching mask 104 having thickness distribution is left behind only on the recess 103. When the etching further advances from this state, the substrate 101 having a higher etching rate is etched more than the etching mask 104. The point angle of the needle can be controlled by the etching selectivity ratio between the etching mask 104 and substrate 101 (the ratio of the etching rate of the etching mask to the etching rate of the substrate). The point angle of the needle becomes sharp with an increased height when the etching selectivity ratio is high. The point angle of the needle becomes dull with a decreased height when the etching selectivity ratio is low.

As shown in FIG. 1D, if the etching is stopped at the state having a remaining etching mask and the remaining etching mask is stripped off, a needle having a recess corresponding to the shape of the bottom of the recess at the tip may be manufactured. The needle having such a recess at the tip is favorable for use in, for example, sampling the blood and injecting a drug solution.

Figure 1F:
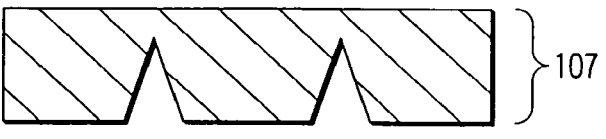

By using the microneedle 106 manufactured as shown in FIG. 1E as a master mold, a replica mold 107 may be manufactured (FIG. 1F). Any materials may be used as the material of the replica mold 107 as long as they have appropriate shape adaptability and hardness, and examples thereof include plated metals and molding resins such as organic silicones.

The metal plating method will be described below. A metal layer is uniformly formed by plating over the entire surface of the microneedle 106 used as the master mold. Then, the microneedle 106 used as the master mold is removed to form a replica mold 107 made of the metal.

Although the thickness of the metal film formed is not limited, it is preferably twice or more as thick as the height of the needle. The type of the metal is not particularly limited, and nickel, copper and various alloys may be favorably used.

Ceramics and resins may be used other than the metal materials. Examples of the method for depositing the film include plating as well as plasma deposition, sputtering, CVD, evaporation, sintering and casting.

Subsequently, the replica mold 107 is used for transcription to various materials. The microneedle is replicated by imprinting, hot-embossing, injection molding or casting with the use of the replica mold 107. Although the material of the replicated product is not particularly limited, a biocompatible microneedle may be formed by using a biocompatible material such as a medical use silicone resin, maltose, polylactic acid, dextran or chitin-chitosan.

Modified Example of FIGS. 1A to 1F

The etching mask is formed on the entire surface of the substrate in FIG. 1C, but varying the pattern of the etching mask enables to manufacture a microneedle having various shapes. Embodiments in which the pattern of the etching mask is varied will be described.

Figure 2A:
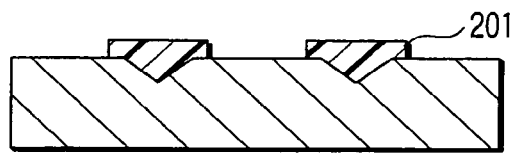
FIGS. 2A and 2B show examples of needles which can be formed by the manufacturing method according to the invention.
Figure 2B:
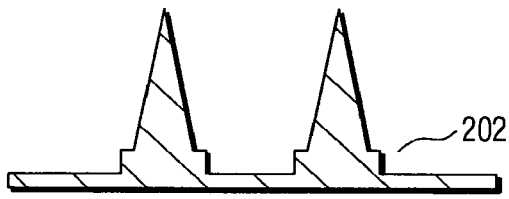

As shown in FIG. 2A, a pattern of an etching mask 201 that covers the recess 103 and a part of the periphery of the recess 103 may be formed. In this case, as shown in FIG. 2B, a microneedle 202 having a reinforced bottom part may be manufactured by etching.

Since the bottom of the microneedle receives large stress when the needle is stabbed, an effect that the needle is hardly broken in stabbing may be obtained if the needle has the reinforced bottom part.

Figure 3A:
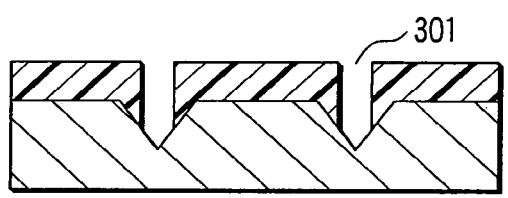
FIGS. 3A and 3B show examples of needles which can be formed by the manufacturing method of the invention.
Figure 3B:
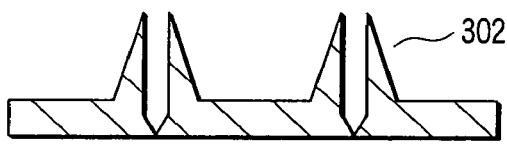

An opening 301 that corresponds to the center of the recess 103 may be provided on the etching mask 104 formed on the entire surface of the substrate as shown in FIGS. 1A to 1F and 3A. Since the center of the bottom of the recess 103 corresponding to the opening 301 of the etching mask 104 is etched faster as shown in FIG. 3B, a microneedle 302 having a hollow part is formed. The microneedle 302 having the hollow part has a shape favorable for sampling of the blood and injection of a drug solution.

The center of the recess 103 and the center of the opening 301 may be displaced from each other within the area of the recess 103. The opening 301 may be provided at a position where no recess 103 is formed.

The height of the microneedle may be readily controlled by changing the thickness of the etching mask. The height of the needle manufactured tends to be larger as the thickness of the etching mask is larger.

Figure 4A:
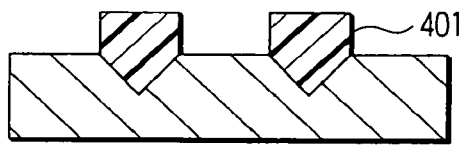
FIGS. 4A and 4B show examples of needles which can be formed by the manufacturing method of the invention.
Figure 4B:
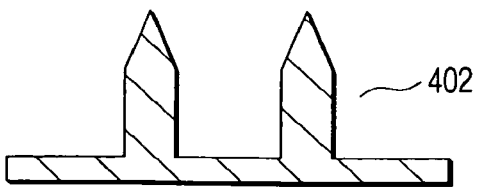

As shown in FIG. 4A, a thick etching mask 401 may be formed only at the position corresponding to the recess 103. In this case, as shown in FIG. 4B, a microneedle whose body is a round column instead of being a cone and which is sharpened only at the tip can be produced by etching. In this manner, it is possible to control the height of the microneedle irrespective of the depth of the recess 103 provided in advance.

The method of manufacturing a microneedle according to another embodiment of the invention will be described below with reference to FIGS. 5A to 5D.

<Process for Forming Etching Mask on the Substrate>

First, an etching mask 102 is formed on the substrate 101 (FIG. 5A).

Any materials may be used for the substrate as long as they can be processed by etching such as plasma etching, and any materials suitable for the processing method may be selected appropriately. Specific examples include silicon, a metal material such as aluminum and stainless steel, and a synthetic resin such as polycarbonate, polystyrene, acrylic resin and fluorinated resin.

The preferred material of the etching mask is required to be adhesive to the substrate, and to have a lower etching rate than the etching rate of the substrate in the etching process described below.

The method for forming the etching mask is required to be able to uniformly form the etching mask on the substrate, and specific examples of the method include CVD (chemical vapor deposition), PVD (physical vapor deposition), spray coating and ejection of droplets.

Any known methods may be appropriately used for forming the pattern of the etching mask. For example, usable methods include a method of exposure and development (where the pattern is controlled by a photomask used) and a method of ejecting a droplet (where the droplet is ejected into the pattern only).

Since the diameter of the needle manufactured depends on the diameter of the etching mask formed, the diameter of the etching mask is adjusted according to the diameter of the desired needle.

An array of etching masks may be formed. Manufacture of a microneedle array is possible by forming the array of the etching masks. The pitch between the needles and the number of the needles may be controlled by adjusting the pattern layout of the etching mask.

<Process for Deforming the Etching Mask so as to have Thickness Distribution>

Next, the etching mask is deformed so as to have thickness distribution (FIG. 5B).

Thin portions of the etching mask are removed faster than thick portions of the etching mask in the etching process described below. Accordingly, the time needed for removing the mask may be controlled by allowing the etching mask to have thickness distribution. Since the substrate is being etched simultaneously, etching of the portion of the substrate corresponding to the portion of the removed mask advances as the mask is removed.

When the thickness of the periphery of the etching mask is reduced relative to the thickness at the central portion of the etching mask, and the thickness of the etching mask is made to continuously change from the periphery to the central portion of the etching mask, the mask is gradually removed from the periphery of the etching mask as etching advances. Thus, a needle having a taper angle depending on the etching selectivity ratio between the substrate and etching mask (the ratio of the etching rate of the substrate to the etching rate of the etching mask) can be manufactured.

Since the time required for removing the mask is controlled by allowing the etching mask to have thickness distribution, the point angle and the height of the needle manufactured may be controlled in the etching process described below. When the mask is etched until the etching mask is eliminated under the same etching condition, the height of the needle manufactured increases as the thickness of the initial etching mask is larger.

The etching mask may be reflowed for deforming the etching mask so as to have thickness distribution. When the etching mask is made to reflow by heating, the thickness of the etching mask smoothly changes owing to surface tension. Thus, the thickness of the etching mask at the periphery is reduced relative to the thickness at the central portion of the etching mask so that the thickness of the etching mask continuously changes from the periphery to the central portion of the etching mask.

The thickness distribution of the etching mask is determined by the reflow condition. Accordingly, when plural etching masks are provided on the substrate in particular, the thickness distribution of the etching masks is made uniform, thereby plural needles may be manufactured in one step with high precision.

The thickness and the thickness distribution of the etching mask after reflow may be adjusted by adjusting the initial thickness of the etching mask and heating temperature.

In performing reflow, the substrate may be heated. The heating method is not particularly limited. For example, the substrate may be heated using a heating device such as an oven or a hot plate.

Alternatively, when the etching mask is formed by ejecting droplets prepared by dissolving a mask material in a solvent or by ejecting droplets prepared by melting the mask material with heating with the use of the droplet ejecting method, the etching mask may be deformed so as to have thickness distribution by allowing the solvent to evaporate or by allowing the mask material to solidify. Even in these methods, the thickness of the etching mask smoothly changes owing to surface tension. Consequently, the thickness of the etching mask may be reduced at the periphery relative to the thickness at the central portion of the etching mask so that the thickness of the etching mask continuously changes from the periphery to the inner portion of the etching mask.

The etching mask may be formed in an arbitrary shape within the range of accuracy of ejection of droplets when the etching mask is formed by ejecting the droplets.

The thickness distribution of the etching mask is determined by the evaporation condition of the solvent or solidification condition. Accordingly, when plural etching masks are formed on the substrate, the thickness distribution of each etching mask may be uniform, thereby plural needles may be manufactured with high precision in one step.

When the solvent is evaporated or the mask material is solidified, the substrate is heated or placed under a reduced pressure, or heated under a reduced pressure. The evacuation method and heating method are not particularly limited, and a heating device such as an oven or a hot plate operated under a reduced pressure may be used.

<Process for Etching>

The entire substrate on which the etching mask has been formed is further etched (FIG. 5C) to manufacture the microneedle (FIG. 5D).

The etching method may be any methods as long as the method uses anisotropic etching in which the etching rate of the substrate is different from the etching rate of the etching mask, and any known methods may be appropriately used. For example, dry etching with a dry etching apparatus using discharge methods such as RIE, magnetron RIE, ECR, ICP, NLD, microwave and helicon wave.

When the thickness of the etching mask is continuously changed from the periphery to the central portion of the mask so that the thickness at the periphery of the etching mask is smaller than the thickness at the central portion of the etching mask, the etching mask is gradually removed from the periphery of the etching mask as etching advances. Consequently, microneedles having a taper angle depending on the etching selectivity ratio between the substrate and etching mask (the ratio of the etching rate of the substrate to the etching rate of the etching mask) may be manufactured.

Figure 7A:
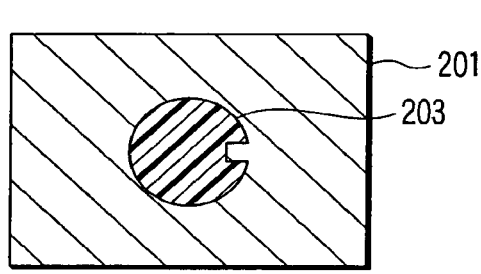
FIGS. 7A and 7B show an example of a needle which can be formed by the method of manufacturing the microneedle according to the invention.

The etching mask may be inwardly depressed at least at a part of the periphery. Examples of the shape of the etching mask having a periphery that is inwardly depressed at least at a part thereof include a cross-shaped etching mask 202 formed on the substrate 201 as shown in FIG. 6A, or an etching mask 203 having a circular bottom a part of which is inwardly depressed and formed on the substrate 201 as shown in FIG. 7A. Other examples include a star-like shape in which the bottom has an arbitrary number of apexes, which are connected with continuous straight lines or curved lines.

Figure 7B:
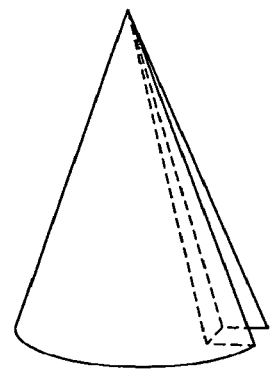

When at least a part of the periphery of the etching mask is inwardly depressed, a depression is formed on the sidewall of the needle as shown in FIGS. 6B and 7B after etching, thereby the surface area of the needle may be increased. Consequently, a needle having a shape suitable for holding and injecting a drug solution may be manufactured.

Since the taper angle of the needle is determined by the etching selectivity ratio between the substrate and etching mask as described above, the taper angle and point angle of the needle may be designed and manufactured without limiting the material of the substrate to a single crystal material.

The point angle of the needle can be controlled by the etching selectivity ratio of the substrate to the mask. The point angle of the needle tends to be sharpened with a larger height of the needle when the etching selectivity ratio is higher, while the point angle tends to be dull with a smaller height of the needle when the etching selectivity ratio is lower.

Since the mask is gradually removed and the needle is formed by completely removing the mask after the mask has been finally converged into a fine area, a needle having a sharp tip may be manufactured without being contaminated with stripped etching mask.

The etching may stopped at a state that the etching mask is still left behind (FIG. 5C), and then the mask may be stripped off. A needle having a flat portion only at the tip of the needle may be manufactured. Such needle is able to reduce break of the tip when the needle is stabbed.

The etching condition may be changed so that the etching selectivity ratio of the substrate to the etching mask is changed on the way of etching.

Since the taper angle is determined by the etching selectivity ratio as described above, a needle having a taper angle that changes stepwise may be manufactured by changing the etching condition on the way of etching.

The etching selectivity ratio that is a value provided by dividing the etching rate of the substrate to be etched by the etching rate of the etching mask is preferably from 1 or more to 100 or less. An etching selectivity ratio from 5 or more to 50 or less is particularly preferable for precisely transcribing the shape of the etching mask to the substrate.

However, the etching selectivity ratio is not limited to the above-mentioned range, and may be appropriately changed depending on the desired taper angle of the needle. For example, a very large selectivity ratio (100 or more) may be used when the etching condition is changed on the way of etching.

Figure 8A:
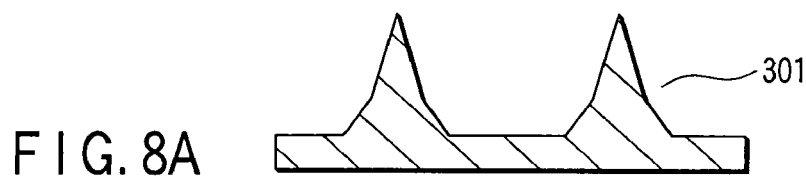
FIGS. 8A to 8C show examples of needles which can be formed by the method of manufacturing the microneedle according to the invention.

When etching starts with a smaller etching selectivity ratio and the etching selectivity ratio is increased thereafter, the bottom of the needle becomes to have a gentle taper angle so that a needle having a reinforced shape at the bottom where the needle receives large stress in stabbing may be manufactured. Such a needle exhibits an effect that makes the needle hardly broken in stabbing (FIG. 8A).

Figure 8B:
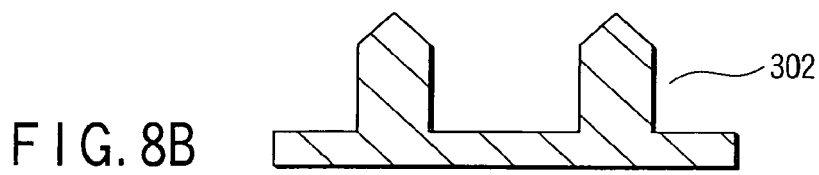

When the etching selectivity ratio is made very high, the sidewall of the needle may be made to have an approximately vertical angle since the etching rate of the substrate is quite higher relative to the etching rate of the etching mask. Accordingly, a needle having a high aspect ratio may be manufactured while the diameter of the bottom part is kept constant (FIG. 8B). In particular, in the case of an array having arranged needles, a high aspect ratio is effective since the needles may be densely disposed.

Figure 8C:
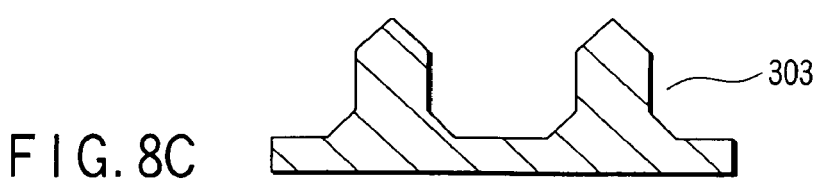

The etching condition may be changed with a combination of the etching conditions. The combination of changes of the etching conditions permits a needle having a gentle slope at the bottom and a high aspect ratio to be manufactured (FIG. 8C).

As described above, the needle can be manufactured by a simple manufacturing process in which the point angle and the height of the needle can be readily controlled.

The method of manufacturing a needle having a hole or penetrated hole will be described below with reference to FIGS. 9A to 9D and 10A to 10D.

<Process for Forming a Hole on the Substrate>

Figure 9A:
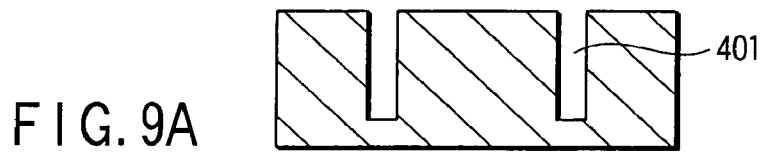
FIGS. 9A to 9D show cross-sectional views showing a method of manufacturing a microneedle according to the invention.

First, a hole 401 is formed on the substrate (FIG. 9A). If the hole 401 is provided at a position corresponding to the etching mask of the substrate 101 in advance, a hollow needle may be manufactured. The needle having such a shape is favorable, for example, for sampling the blood and for injecting a drug solution.

Any known methods may be appropriately used for forming the hole 401 on the substrate depending on the shape, dimension and degree of integration of the needle. Example of the method include deep etch by etching, laser processing and other precise machining.

Figure 10A:
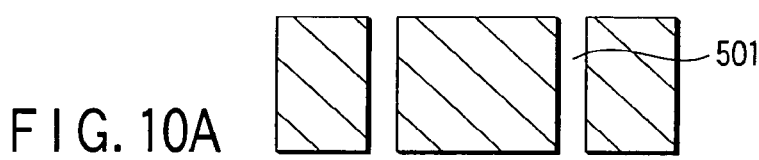
FIGS. 10A to 10D show cross-sectional views showing a method of manufacturing a microneedle according to the invention.

A hole 501 that penetrates the substrate may be formed (FIG. 10A). A needle having a penetrated hole may be manufactured by providing the hole 501 that penetrates the substrate.

<Process for Filling the Hole with a Filler>

Figure 9B:
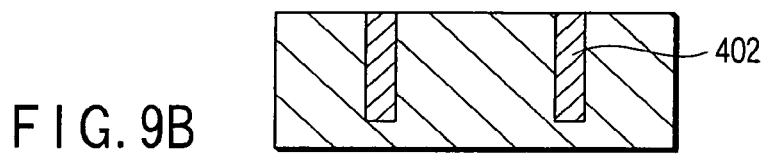
Figure 10B:
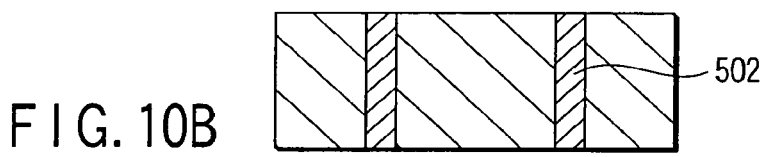

Next, the hole 401 or 501 provided on the substrate is filled with a filler 402 or 502 (FIG. 9B or 10B).

Any filler may be used as long as it is able to fill the hole having a size from several μm to hundreds of μm. Examples of the filler include a metal material such as Ni, silicone and a heat resistant resin.

Any known methods may be appropriately used for filling with the filler. Examples of the method include plating such as electroplating and filling the hole with a molten material.

<Process for Forming an Etching Mask Having Thickness Distribution at a Portion Corresponding to the Hole and Process for Etching>

Figure 9C:
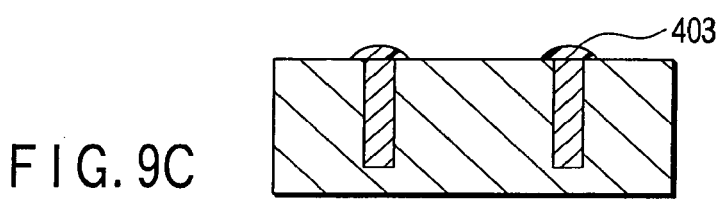
Figure 10C:
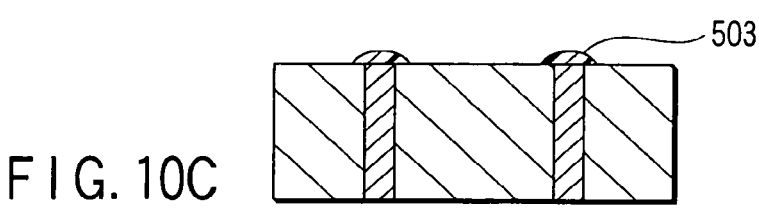

Next, an etching mask having thickness distribution is formed at the portion corresponding to the hole (the etching mask 403 or 503), and etching is performed (FIG. 9C or 10C).

These processes may be implemented by the same method as described above.

<Process for Removing the Filler>

Figure 9D:
Figure 10D:
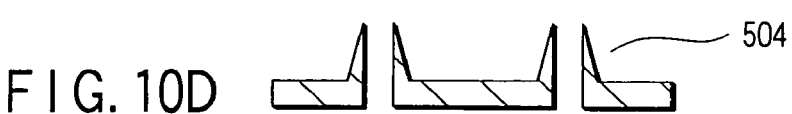

The needle 404 or 504 is provided by removing the filler 402 or 502 (FIG. 9D or 10D).

Any methods may be available as long as the filler can be removed without heavily damaging the substrate. For example, the filler may be dissolved by using various etching solutions or solvents suitable for the selected filler.

Another embodiment of a method of manufacturing the needle by providing a penetrated hole will be described below with reference to FIGS. 11A to 11C.

<Process for Forming a Hole on the Substrate>

Figure 11A:
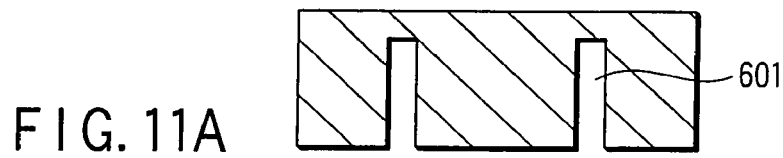
FIGS. 11A to 11C show cross-sectional views showing a method of manufacturing a microneedle according to the invention.

First, a non-penetrated hole 601 is formed on the substrate (FIG. 11A). The substrate used and the method for forming the hole are the same as described above.

<Process for Forming an Etching Mask on a Side of the Substrate Opposed to the Side where the Hole is Provided, and for Deforming the Etching Mask so as to have Thickness Distribution>

Figure 11B:
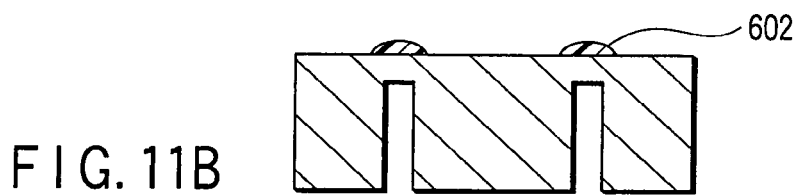

Next, an etching mask 602 is formed on the side of the substrate opposed to the side where the hole 601 is provided, and the etching mask 602 is deformed so as to have thickness distribution (FIG. 11B). The method for forming the etching mask and for deforming the mask so as to have thickness distribution is the same as described above.

When the etching mask 602 corresponding to the hole is formed on another side of the substrate opposed to the side where the hole is provided, a needle having a penetrated hole can be manufactured without filler.

<Process for Etching>

Figure 11C:
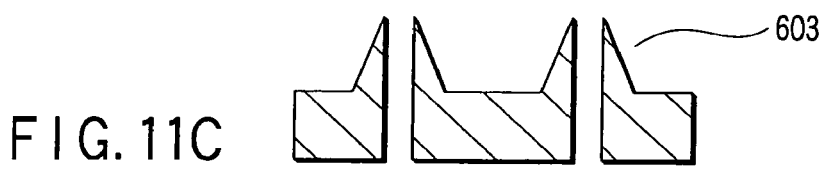
Figure 12A:
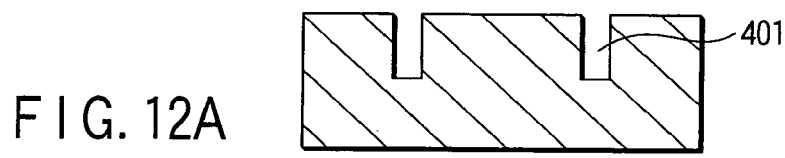
FIGS. 12A to 12D show cross-sectional views showing a method of manufacturing a microneedle according to the invention.
Figure 12B:
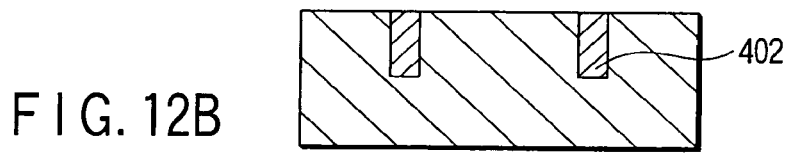
Figure 12C:
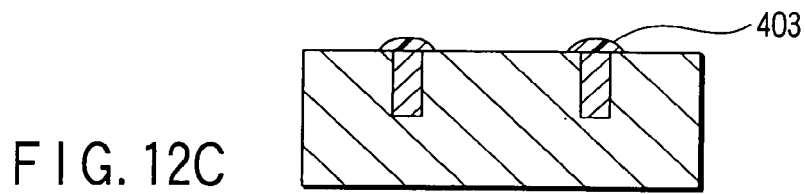
Figure 12D:
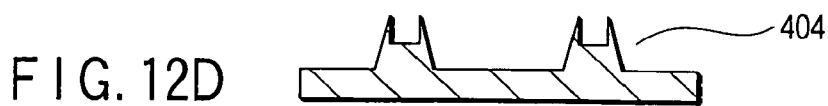
Figure 13A:
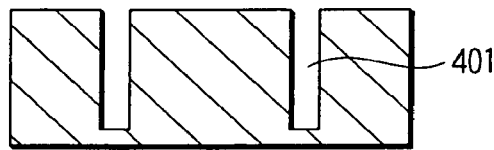
FIGS. 13A to 13D show cross-sectional views showing a method of manufacturing a microneedle according to the invention.
Figure 13B:
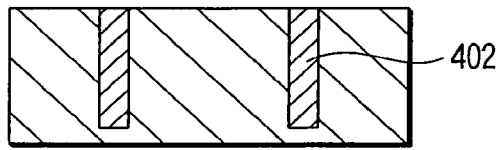
Figure 13C:
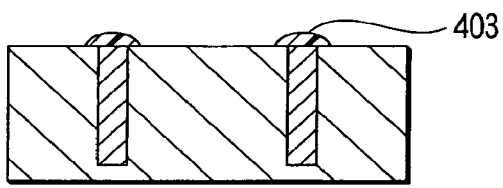
Figure 13D:
Figure 14A:
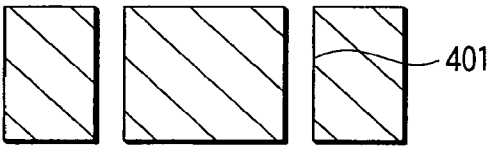
FIGS. 14A to 14D show cross-sectional views showing a method of manufacturing a microneedle according to the invention.
Figure 14B:
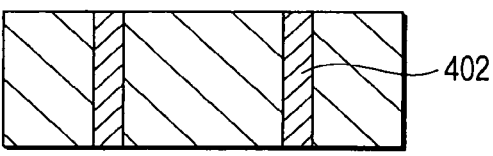
Figure 14C:
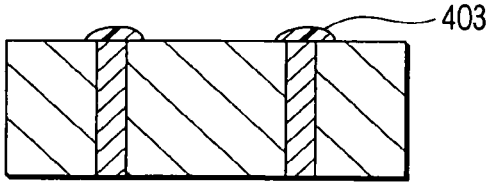
Figure 14D:
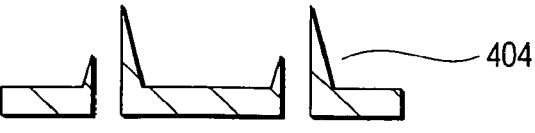
Figure 15A:
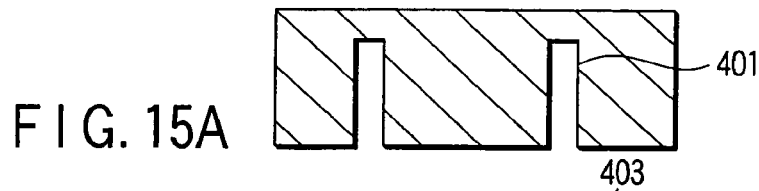
FIGS. 15A to 15C show cross-sectional views showing a method of manufacturing a microneedle according to the invention.
Figure 15B:
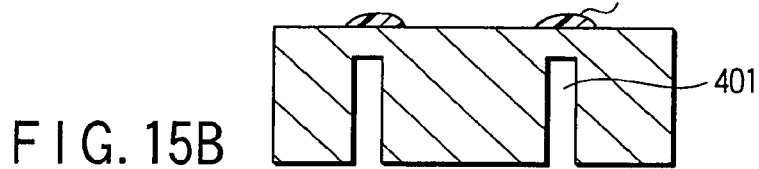
Figure 15C:
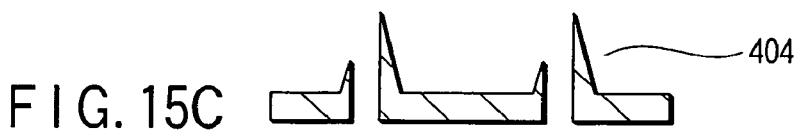
Figure 16A:
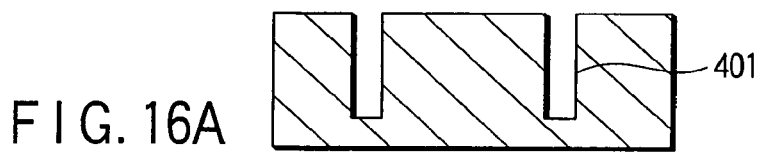
FIGS. 16A to 16D show cross-sectional views showing a method of manufacturing a microneedle according to the invention.
Figure 16B:
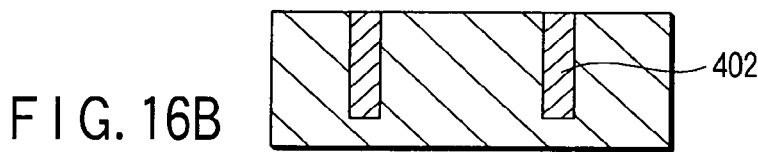
Figure 16C:
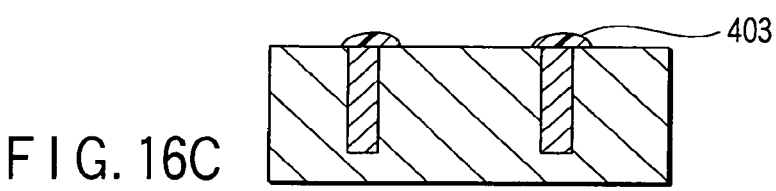
Figure 16D:
Figure 17A:
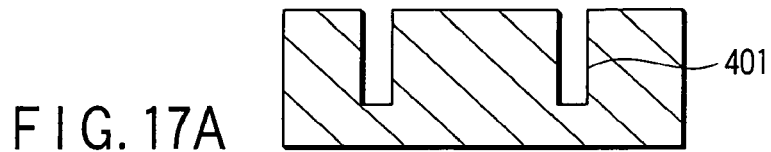
FIGS. 17A to 17D show cross-sectional views showing a method of manufacturing a microneedle according to the invention.
Figure 17B:
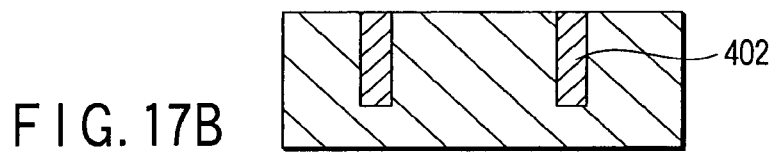
Figure 17C:
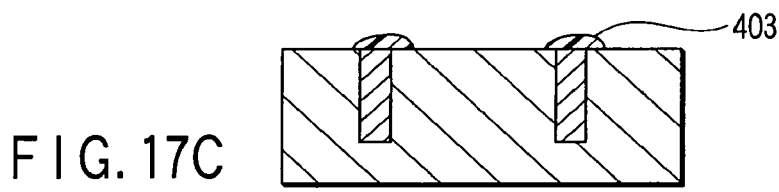
Figure 17D:
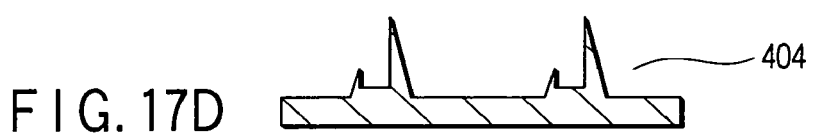
Figure 18A:
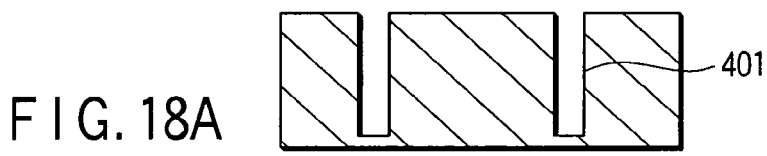
FIGS. 18A to 18D show cross-sectional views showing a method of manufacturing a microneedle according to the invention.
Figure 18B:
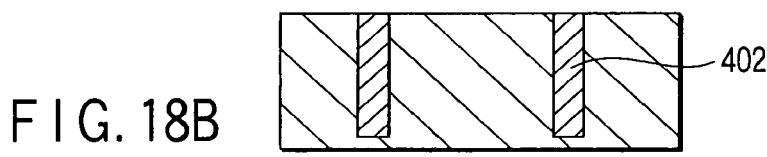
Figure 18C:
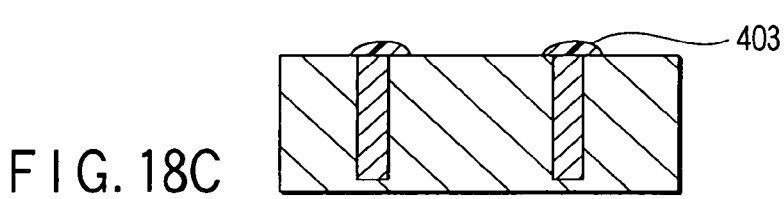
Figure 18D:
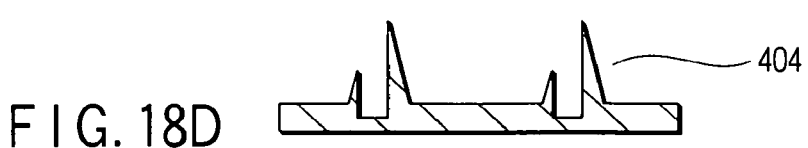
Figure 19A:
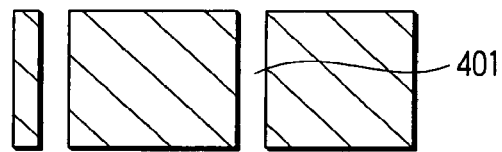
FIGS. 19A to 19D show cross-sectional views showing a method of manufacturing a microneedle according to the invention.
Figure 19B:
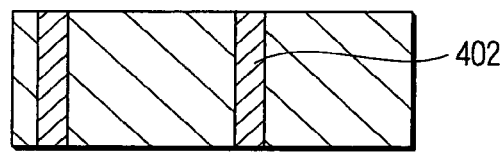
Figure 19C:
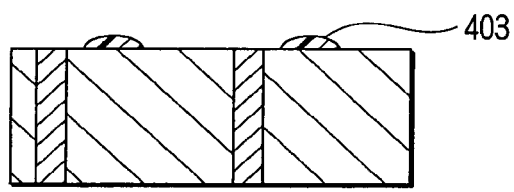
Figure 19D:
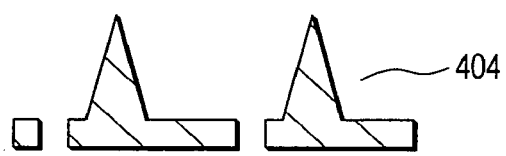

Next, etching is performed to manufacture a needle 603 having a penetrated hole (FIG. 11C). This process can also be performed as described above.

A hollow needle is produced by the method as described above. Such a hollow needle has a shape favorable for sampling the blood and for injecting a drug solution.

Modified Example of FIGS. 9A to 9D

The depth of the hole is approximately the same as the depth of etching in FIGS. 9A to 9D, but the relation between the depth of the hole and the depth of etching can be appropriately adjusted.

FIGS. 12A to 12D show an example in which the substrate is etched deeper than the depth of the hole.

FIGS. 13A to 13D show an example in which the substrate is etched shallower than the depth of the hole.

Modified Example of FIGS. 10A to 10D

The center of the hole and the center of the etching mask are aligned with each other in FIGS. 10A to 10D, but the center of the hole and the center of the etching mask may be slightly displaced from each other.

FIGS. 14A to 14D show an example in which the center of the hole and the center of the etching mask are slightly displaced from each other. An opening having an inclined plane is formed at the tip of the needle in this example.

Modified Example of FIGS. 11A to 11C

The center of the hole and the center of the etching mask formed on the opposite side of the substrate are aligned with each other in FIGS. 11A to 11C, but the center of the hole the center of the etching mask formed on the opposite side of the substrate may be slightly displaced from each other.

FIGS. 15A to 15D show an example in which the center of the hole and the center of the etching mask are slightly displaced from each other. An opening having an inclined plane is formed at the tip of the needle also in this example.

Modified Example of FIGS. 9A to 9D

The center of the hole and the center of the etching mask are aligned with each other in FIGS. 9A to 9D, but the center of the hole and the center of the etching mask may be slightly displaced from each other.

FIGS. 16A to 16D show an example in which the center of the hole and the center of the etching mask are slightly displaced from each other. An opening having an inclined plane is also formed at the tip of the hollow needle in this example.

Modified Example of FIGS. 16A to 16D

The depth of the hole is approximately the same as the depth of etching in FIGS. 16A to 16D, but the relation between the depth of the hole and the depth of etching can be appropriately adjusted.

FIGS. 17A to 17D show an example in which the substrate is etched deeper than the depth of the hole.

FIGS. 18A to 18D show an example in which the substrate is etched shallower than the depth of the hole.

Modified Example of FIGS. 10A to 10D

The center of the hole and the center of the etching mask are aligned with each other in FIGS. 10A to 10D, but the hole and the etching mask may be displaced from each other so that they are not overlapped.

FIGS. 19A to 19D show an example in which the hole and the etching mask are displaced from each other so that they are not overlapped. The penetrated hole is formed remote from the position of the needle in this example.

Modified Example of FIGS. 11A to 11C

The center of the hole is aligned with the center of the etching mask formed on the opposed side of the substrate, but the hole and the etching mask may be displaced from each other so that they are not overlapped.

Figure 20A:
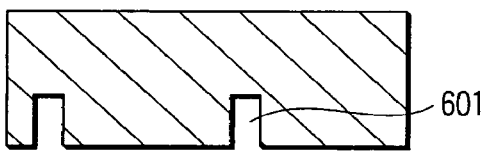
FIGS. 20A to 20C show cross-sectional views showing a method of manufacturing a microneedle according to the invention.
Figure 20B:
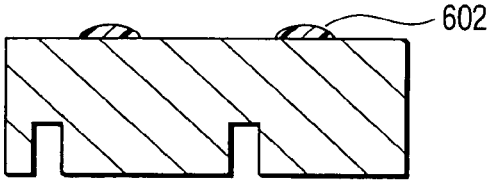
Figure 20C:
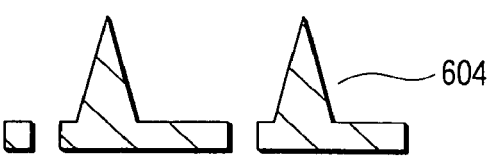

FIGS. 20A to 20C show an example in which the hole and the etching mask are displaced from each other so that they are not overlapped. The penetrated hole is formed remote from the position of the needle also in this example.

Modified Example of FIGS. 20A to 20C

Although the non-penetrated hole is formed in FIGS. 20A to 20C, a penetrated hole may be provided when the hole and the etching mask are displaced from each other so that they are not overlapped.

Figure 21A:
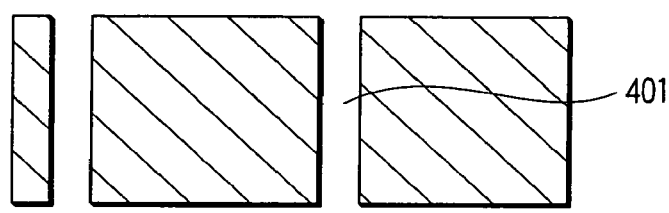
FIGS. 21A to 21C show cross-sectional views showing a method of manufacturing a microneedle according to the invention.
Figure 21B:
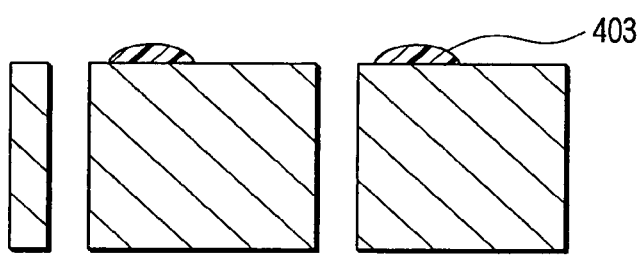
Figure 21C:
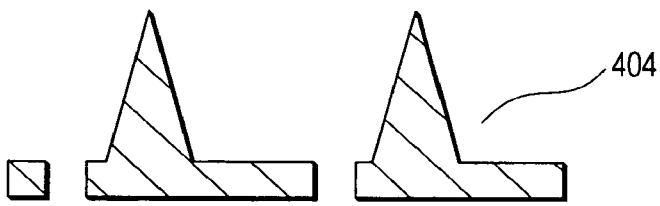

FIGS. 21A to 21C show an example in which the penetrated hole and the etching mask are displaced from each other so that they are not overlapped. The penetrated hole is formed remote from the position of the needle also in this case.

In any of the above-mentioned examples, isotropic etching may be further applied after forming the needle. FIGS. 22A to 22C show an example in which the needle once formed is subjected to isotropic etching. When the needle in FIG. 22A is subjected to isotropic etching, the entire shape of the needle is uniformly contracted by a given length as shown in FIG. 22B. Consequently, the bottom of the needle is rounded while the tip of the needle is sharpened as shown in FIG. 22C. The isotropic etching performed in this manner can adjust the shape of the needle such that the needle is made to be ready for stabbing and hardly broken.

Transcription of the needle will be described below with reference to FIGS. 23A to 23D.

A replica mold 703 is formed by using the microneedle 701 manufactured by the above-mentioned method as a master mold.

First, the replica mold 703 is formed on the surface on which the needle 701 is formed (FIG. 23A).

Although the material of the replica mold 703 is not particularly limited, it is selected in terms of shape adaptability for serving as the replica mold, transcription ability in the transcription process described below, durability and releasing ability. For example, nickel may be used as the material of the replica mold 703. In this case, the method of forming the nickel film includes plating, PVD and CVD.

Then, the replica mold 703 is separated from the needle 701 (FIG. 23B).

As the method of separating the replica mold 703 from the needle 701, separation with physical peeling force or selective etching may be used.

Next, the replica mold 703 is filled with a needle material (FIG. 23C).

Although the needle material is not particularly limited, a biocompatible needle may be formed by using a medical silicone resin, maltose, polylactic acid, dextran, chitin or chitosan as a biocompatible material.

Although the method for filling with the needle material is not particularly limited, imprinting, hot-embossing, injection molding, extrusion molding or casting may be favorably used in terms of productivity.

Next, the needle material is released from the replica mold 703 to provide a needle 704 formed by transcription molding (FIG. 23D).

For improving peeling property from the replica mold 703, a release layer (not shown) for enhancing releasing effect may be formed on the surface of the replica mold 703 prior to filling with the needle material.

As the release layer, widely known fluorinated resins, for example, may be used. As the method for forming the release layer, PVD, CVD, spin coating or dip coating may be favorably used.

The transcription of the needle can be performed as described above. Since mass production of needles can be implemented using the same replica mold by manufacturing a replica mold having a high mechanical strength which is integrally molded, the needles may be produced under low production cost with high productivity.

Other embodiments of the invention will be described below with reference to FIGS. 24A to 24F and 25A and 25B.

FIGS. 24A to 24D show a process for manufacturing a microneedle of this embodiment, and FIGS. 24E and 24F show a process for manufacturing a replica mold using the microneedle as a master mold.

First, as shown in FIG. 24A, a negative resist is applied to the surface of a substrate 13 to form a resist layer 12.

Then, the resist layer 12 is exposed into a pattern of the microneedles by photolithography using a mask 15. The mask 15 is this embodiment is formed by providing a needle pattern array in which needle-shaped unit masks 16 schematically shown in FIGS. 25A and 25B are regularly arrayed as shown in FIG. 25A, the unit mask having halftone dots provided such that the number thereof is varied so as to be reduced from the periphery toward the center of the circle. When development is carried out after exposure, the negative resist on non-exposed portions is removed in accordance with the exposure pattern, and projected conical etching masks 17 are formed on the substrate 13 as shown in FIG. 24B.

Subsequently, the etching mask is etched back by reactive ion etching (RIE) as shown in FIG. 24C to form microneedles 14 having a desired height on the substrate 13 (etch process). The materials for the resist layer 12 and substrate 13 and the etching environment are adjusted so that the etching selectivity ratio, which is defined by dividing the etching rate of the substrate 13 per unit time by the etching rate of the resist layer 12, is set from 1 or more to 10 or less, preferably from 1 or more to 5 or less.

If the etching selectivity ratio is larger than 11, the control accuracy for the microneedle 14 is reduced. If the etching selectivity ratio is smaller than 1, a resist layer 12 having an unnecessarily large thickness is to be formed, leading to lowered manufacturing efficiency.

Accordingly, the thickness of the resist layer 12 formed in the above-mentioned process is set to a value defined by dividing the height of the microneedle manufactured by a predetermined etching selectivity ratio.

Upon completion of the etching process, the etching masks 17 are completely removed as shown in FIG. 24D, thereby providing a microneedle array 11 in which projected microneedles 14 having a desired height are formed on the surface of the substrate 13.

The method of manufacturing a microneedle in this embodiment enables to manufacture the microneedle array 11 with a far less number of steps than in the prior art by using a stable substrate such as silicon.

If a thick resist layer 12 is formed using dip coating or an application method, the etch-back etching rate can be set to a relatively low range of 1 or more to 10 or less in the etching process. Consequently, microneedles may be manufactured with highly controlled precision.

Further, by transcribing the microneedle array 11 of this embodiment onto a resin or metal material 18 as shown in FIG. 24E, a replica mold 19 for manufacturing a microneedle may be readily manufactured as shown in FIG. 24F. In such a manner, the replica mold for manufacturing the microneedle can be manufactured by a relatively small number of steps by selecting an optimum material. Any method may be used for transcription that is used in the prior art such as plating, a resin process or a ceramic process. Further, by processing a biocompatible material using the above-mentioned replica mold, a microneedle patch of the invention can be manufactured. Also, if a microneedle is manufactured to have a hole inside and the amount of use of the biocompatible material is adjusted, a microneedle in a single body that is not integrated with a base and is able to be used for an injection syringe can be manufactured.

Although the microneedle array 11 is manufactured by using the negative resist in this embodiment, if a positive resist is used in place of the negative resist, a microneedle formed of the material of the substrate 13 can be provided through an etching process. Accordingly, it is possible to manufacture the microneedles made of a more stable material than a photosensitive material with a fewer steps and to directly manufacture a microneedle patch using the microneedle.

Although the embodiments of the invention have been described above, the technical scope of the invention is not limited to the above-mentioned embodiments, and various modifications are possible within a range not departing from the spirit of the invention.

For example, the resist layer is exposed using a halftone dot mask or a gray scale mask in the processes of exposure and development in the above-mentioned embodiments. However, in place of the above-mentioned masks, the resist layer may be exposed by multiple exposure of the laser beam depending on an integrated exposure value with digitally adjusted exposure value by laser scanning based on the stereoscopic shape of the microneedle to be manufactured.

The microneedle is formed in a circular conic shape or pyramidal shape in the above embodiments, but the shape of the microneedle is not limited to these shapes. The microneedle and replica mold may be manufactured by forming a microneedle having a triangular pyramidal shape or polygonal pyramidal shape.

The coating layer is etched-back by reactive ion etching in the etching process in the above embodiments, but the etching method is not limited thereto. For example, any methods known in the art such as ion etching, ion-beam etching and reactive ion-beam etching may be also used.

Although the microneedle patch is manufactured by injecting a molten biocompatible material into the microneedle or the replica mold for manufacturing a microneedle in the above embodiments, the microneedle patch may be manufactured by using commonly used plastic molding methods such as compression molding and injection molding in place of the methods described above.

EXAMPLES

Example 1

First, a silicon wafer was prepared as a substrate. The silicon wafer had crystal orientation of (100) and a thickness of 525 mm. A chromium film with a thickness of 100 nm was formed on the silicon wafer by DC magnetron sputtering. The sputtering pressure was 0.25 Pa and the input power was 1000 W.

A positive resist (trade name: OFPR-50 cp, manufactured by Tokyo Ohka Kogyo Co., Ltd.) was applied to the chromium film as an etching mask in a thickness of 1 mm. A resist pattern with an opening of 50 mm square was formed by photolithography. The chromium film was etched with a mixed solution of perchloric acid and cerium (IV) ammonium sulfate using the resist pattern as an etching mask to form a chromium pattern having an opening of 50 mm square. After formation of the chromium pattern, the resist pattern was removed with an organic solvent. The size of the opening of the chromium pattern was measured to be 51 mm square (FIG. 4A).

The silicon wafer was subjected to anisotropic wet etching with an aqueous potassium hydroxide solution at a concentration of 25% by weight and at a temperature of 90° C. by using the chromium pattern as an etching mask and by taking advantage of the difference in the etching rate depending on the crystal orientation to form a recess on the surface of the silicon wafer (FIG. 1B). After the wet etching, the chromium pattern was removed with a mixed solution of perchloric acid and cerium (IV) ammonium sulfate. The shape of the recess formed on the surface of the silicon wafer was observed with a scanning electron microscope to have a depth of about 35 mm and an angle of opening at a deepest portion of 70°. The angle of opening as used herein refers to an angle between opposed sidewalls of a pyramidal shape.

A positive resist (trade name: OFRP-800, manufactured by Tokyo Ohka Kogyo Co., Ltd.) was applied to the entire surface of the silicon wafer in a thickness of 50 mm. As a result, the resist layer filled in the recess on the surface of the silicon wafer had thickness distribution. The entire surface of the silicon wafer was etched by ICP (inductively coupled plasma) etching using a fluorine-base gas until the resist was completely removed. The etching selectivity ratio between the etching rates of the resist and silicon was measured to be about 11.

When the sample subjected to etching was observed with a scanning electron microscope, it was confirmed that a pyramidal needle with a bottom side length of 50 mm, a height of about 350 mm and a point angle of about 8.2° was formed.

A nickel layer with a thickness of 300 nm was deposited by evaporation on the silicon wafer on which the pyramidal needle was formed. A nickel layer with a thickness of 1 mm was formed by electroplating using the above-mentioned nickel layer as a seed layer. Then, silicon was dissolved with an aqueous potassium hydroxide solution at a concentration of 25% and at a temperature of 90° C. to manufacture a replica mold made of nickel according to the invention.

Transcription was performed to maltose, dextran, chitin-chitosan, or polylactic acid by imprinting using the replica mold. It was confirmed that a needle with a bottom side length of about 50 mm, a height of about 350 mm and a point angle of about 8.2° was formed as formed on the silicon master mold by using any of the replication materials.

Example 2

An example of manufacturing a microneedle using an etching mask having a circular dot pattern will be described.

First, a silicon wafer (thickness: 525 mm) was prepared as a substrate. A thick photoresist for general purpose (trade name: AZ PLP, manufactured by Clariant Co.) was applied to the silicon wafer as an etching mask in a thickness of 13 mm by spray coating. Etching masks having a circular dot pattern with a diameter of 100 mm was formed by photolithography.

Then, the etching masks were reflowed by heating the silicon wafer at 150° C. for 30 minutes in a clean oven. The resist pattern after reflow had a cross-sectional shape of a hemisphere and a thickness at the central portion of 20 mm.

Subsequently, the entire surface of the silicon wafer was etched by ICP (inductively coupled plasma) etching using a fluorine-base gas until the resist pattern was completely removed. As a result of measurement of the etching rates of the resist and silicon substrate, it was found that the etching selectivity ratio of the silicon to the etching mask was about 11.

The silicon wafer subjected to etching was observed with a scanning electron microscope. It was confirmed that a circular conical needle with a diameter of the base portion of about 100 mm, a height of about 220 mm and a point angle of about 25° was formed.

Example 3

A microneedle was manufactured as in Example 2. It should be noted that a pyramidal etching mask having a cross-shaped bottom part as shown in FIGS. 2A and 2B was used. The shape of the bottom of the etching mask was a cross formed by allowing two lines with a width of 40 mm and a length of 150 mm to intersect at right angles. The thickness of the etching mask was 18 mm at maximum.

The silicon wafer subjected to etching was observed with a scanning electron microscope as in Example 2. A pyramidal needle having a cross-shaped bottom part formed by allowing two lines with a width of 40 mm and a length of 150 mm to intersect at right angles and a height of about 200 mm was provided.

Example 4

A microneedle was manufactured as in Example 2. It should be noted that a circular conical etching mask with a part of the circular bottom depressed as shown in FIGS. 3A and 3B. The shape of the bottom of the etching mask was formed by cutting a portion with a width of about 10 mm and a length of about 10 mm from the periphery to the center of a circle with a diameter of 100 mm. The thickness of the etching mask was 19 mm at maximum.

The silicon wafer subjected to etching was observed with a scanning electron microscope as in Example 2. A circular conical needle having a bottom shape in which a portion with a width of about 10 mm and a length of about 10 mm was cut from the periphery to the center of a circle with a diameter of 100 mm and a height of 210 mm was provided.

Example 5

An example of manufacturing a hollow microneedle will be described.

A silicon wafer (thickness: 525 mm) was prepared as a substrate. A hole with a diameter of 20 mm and a depth of 200 mm was provided by perpendicular deep etching on the silicon wafer at a position corresponding to the center of an etching mask to be formed.

Then, a copper thin film with a thickness of 100 nm was deposited on the surface of the substrate and on the wall of the hole by DC magnetron sputtering. The deposition pressure was set to 0.25 Pa. The copper film was used as a seed layer for electroplating performed in the next step. A copper film with a thickness of 300 mm was deposited by electroplating to fill the hole. A copper sulfate bath (copper sulfate 80 g/L, sulfuric acid 200 g/L) was used as the plating solution, the temperature of which was set to room temperature.

The plated substrate was then subjected to planarization treatment by chemical mechanical polishing until the surface of the substrate was exposed for planarizing the surface roughness.

Then, formation of the etching mask pattern, reflow and etching were performed as in Example 2.

Subsequently, copper filled in the hole was removed by immersing the substrate in an ferric chloride solution (30% $FeCl_3$, 3% HCl) for 2 hours.

The needle formed had an outer shape of a circular conical shape with a bottom diameter of about 100 mm and a height of about 175 mm having a hollow part with a diameter of 20 mm and a depth of 155 mm at the center.

Example 6

An example of manufacturing a microneedle by transcription will be described.

The microneedle manufactured by using the silicon wafer in Example 2 was used as a master mold. A nickel film with a thickness of 300 nm was deposited on the surface of the master mold by evaporation. A nickel film with a thickness of 1 mm was formed by electroplating using the nickel layer as a seed layer. Then, the silicon wafer was dissolved with an aqueous potassium hydroxide solution with a concentration of 25 wt % at a liquid temperature of 90° C. to manufacture a replica mold made of nickel.

Transcription was performed to maltose, dextran, chitin-chitosan, or polylactic acid by imprinting using the replica mold. As a result, it was confirmed that a needle similar to the master mold was formed with any of the materials.

Example 7

An example of adjusting the shape of the microneedle will be described.

A circular conical needle with a diameter of the bottom part of about 100 mm, a height of about 220 mm and a point angle of about 25° was formed on a silicon wafer as in Example 2.

Then, the needle was cleaned with oxygen plasma and hydrofluoric acid, followed by isotropic etching of the needle by about 5 mm with plasma mainly composed of a fluorine-base gas. By performing the isotropic etching, the shape of the needle was changed to a diameter of the bottom part of about 90 mm, a height of about 200 mm and a point angle of about 22°, that is sharpness of the needle was improved.

The method of manufacturing a microneedle of the invention is applicable to medical field as well as to various fields that require fine needles. For example, the method of the invention is useful for manufacturing microneedles used in MEMS devices, medical fields, drug formulation and cosmetics.

What is claimed is:

1. A method of manufacturing a microneedle comprising:
    forming an island etching mask having thickness distribution on a substrate such that the etching mask has a shape that is thicker at a central portion thereof and is thinner at a periphery thereof, wherein forming the etching mask includes:
        forming an island of a mask material on the substrate and heating the island to cause reflowing and deformation of the island so as to obtain the etching mask having the shape that is thicker at a central portion thereof and is thinner at a periphery thereof,
        ejecting a droplet of a solution containing a solvent and a mask material dissolved therein onto the substrate to form an island and causing evaporation of the solvent in the island to obtain the etching mask having the shape that is thicker at a central portion thereof and is thinner at a periphery thereof, or
        ejecting a droplet of a molten mask material onto the substrate to form an island and causing solidification of the island to obtain the etching mask having the shape that is thicker at a central portion thereof and is thinner at a periphery thereof; and subjecting the substrate and the etching mask to etching until the etching mask is eliminated, thereby processing the substrate into a needle by taking advantage of a difference in etching rates between the etching mask and the substrate.

2. The method according to claim 1, wherein the etching is anisotropic etching.

3. The method according to claim 2, wherein the anisotropic etching is selected from the group consisting of ion etching, reactive ion etching, ion-beam etching and reactive ion-beam itching.

4. The method according to claim 1, wherein the island etching mask having thickness distribution on a substrate is formed on a flat substrate.

5. The method according to claim 1, wherein, after the microneedle is formed, the microneedle is subjected to isotropic etching.

6. The method according to claim 1, further comprising:
forming a replica mold for manufacturing a microneedle by using the substrate having the needle as a master mold;
filling the replica mold for manufacturing a microneedle with a needle material; and
releasing the needle material from the replica mold to form a transcribed microneedle.

7. The method according to claim 6, wherein a material of the replica mold comprises a plated metal, resin or ceramic.

8. The method according to claim 1, wherein the etching mask is made of a resist.

9. The method according to claim 1, wherein forming an island of a mask material on the substrate and heating the island to cause reflowing and deformation of the island so as to obtain the etching mask having the shape that is thicker at a central portion thereof and is thinner at a periphery thereof.

10. The method according to claim 9, wherein the etching mask is made of a resist.

11. The method according to claim 1, wherein ejecting a droplet of a solution containing a solvent and a mask material dissolved therein onto the substrate to form an island and causing evaporation of the solvent in the island to obtain the etching mask having the shape that is thicker at a central portion thereof and is thinner at a periphery thereof.

12. The method according to claim 11, wherein the etching mask is made of a resist.

13. The method according to claim 1, wherein ejecting a droplet of a molten mask material onto the substrate to form an island and causing solidification of the island obtain the etching mask having the shape that is thicker at a central portion thereof and is thinner at a periphery thereof.

14. The method according to claim 13, wherein the etching mask is made of a resist.

* * * * *